United States Patent [19]

Gers-Barlag et al.

[11] Patent Number: 5,780,042
[45] Date of Patent: Jul. 14, 1998

[54] SYNERGISTIC LIGHT PROTECTION COMBINATIONS AND COSMETIC AND DERMATOLOGICAL FORMULATIONS COMPRISING SUCH COMBINATIONS

[75] Inventors: Heinrich Gers-Barlag, Kummerfeld; Anja Müller, Hamburg; Gerhard Sauermann, Wiemersdorf; Beate Uhlmann, Hamburg, all of Germany

[73] Assignee: Beiersdorf AG, Hamburg, Germany

[21] Appl. No.: 495,497

[22] PCT Filed: Jan. 29, 1994

[86] PCT No.: PCT/DE94/00078

§ 371 Date: Feb. 8, 1996

§ 102(e) Date: Feb. 8, 1996

[87] PCT Pub. No.: WO94/18942

PCT Pub. Date: Sep. 1, 1994

[30] Foreign Application Priority Data

Feb. 25, 1993 [DE] Germany .................. 43 05 788.8

[51] Int. Cl.$^6$ .................................................. A61K 7/40
[52] U.S. Cl. ...................... 424/401; 424/59; 514/887; 426/72
[58] Field of Search .................. 424/401, 59; 514/887; 426/72

[56] References Cited

U.S. PATENT DOCUMENTS 5,135,946  8/1992  Bertelli ............................. 514/461

Primary Examiner—Thurman K. Page
Assistant Examiner—D. Faullener
Attorney, Agent, or Firm—Sprung Kramer Schaefer & Briscoe

[57] ABSTRACT

Active compound combinations comprising a combination of at least one substance chosen from the group consisting of 2,4-O-furfurylidenesorbitol and alkyl ethers thereof and at least one substance chosen from the group consisting of tocopherols and tocopheryl esters, and cosmetic and dermatological light protection formulations comprising such active compound combinations.

8 Claims, No Drawings

SYNERGISTIC LIGHT PROTECTION COMBINATIONS AND COSMETIC AND DERMATOLOGICAL FORMULATIONS COMPRISING SUCH COMBINATIONS

This application is a continuation of PCT/DE94/00078 published Jan. 29, 1994.

The present invention relates to light protection formulations in particular cosmetic and dermatological light protection agents.

The damaging effect of the ultraviolet component of solar radiation on the skin is generally known. While rays having a wavelength of less than 290 nm (the so-called UVC range) are absorbed by the ozone layer in the earth's atmosphere, rays in the range between 290 nm and 320 nm, the so-called UVB range, cause erythema, simple sunburn or burns of greater or lesser severity.

The narrower range around 308 nm is stated as having the maximum erythema activity of sunlight.

Numerous compounds are known for protection against UVB radiation, these being derivatives of 3-benzylidenecamphor, of 4-aminobenzoic acid, of cinnamic acid, of salicylic acid, of benzophenone and also of 2-phenylbenzimidazole.

It is also important to have filter substances available for the range between about 320 nm and about 400 nm, the so-called UVA range, since its rays can also cause damage. Thus, it has been proved that UVA radiation causes damage to the elastic and collagenic fibres of the connective tissue, which ages the skin prematurely, and that it is to be regarded as the cause of numerous phototoxic and photoallergic reactions. The harmful influence of UVB radiation can be intensified by UVA radiation.

Certain derivatives of dibenzoylmethane are therefore used for protection against rays in the UVA range, the photostability of which derivatives (Int. J. Cosm. Science 10, 53 (1988)) is not adequate.

However, UV radiation can also lead to photochemical reactions, the photochemical reaction products intervening in skin metabolism.

Such photochemical reaction products are chiefly free-radical compounds, for example hydroxy radicals. Undefined free-radical photoproducts which are formed in the skin itself can also display uncontrolled secondary reactions because of their high reactivity. Singlet oxygen, an excited state of the oxygen molecule without free radicals, however, can also occur under UV irradiation, as can short-lived epoxides and many other compounds. Singlet oxygen, for example, is distinguished by an increased reactivity compared with the triplet oxygen usually present (free-radical ground state). Nevertheless, excited, reactive (free-radical) triplet states of the oxygen molecule also exist.

In order to prevent these reactions, antioxidants and/or agents which trap free radicals can additionally be incorporated into cosmetic or dermatological formulations.

The compounds, some of which are mentioned above, which are employed as light protection agents for cosmetic and dermatological light protection formulations are distinguished by a good light protection action. However, they have the disadvantage that it is sometimes difficult for them to be incorporated into such formulations in a satisfactory manner. Furthermore, these compounds are pure UV-absorbing agents and are unsuitable as agents which trap free radicals.

It has already been proposed to employ vitamin E, a substance having a known antioxidative action, in light protection formulations but, here also, the action achieved remains far below that hoped for.

However, it was surprising and not to be foreseen by the expert that active compound combinations comprising a combination of at least one substance chosen from the group consisting of 2.4-O-furfurylidenesorbitol and alkyl ethers thereof and at least one substance chosen from the group consisting of cosmetically or pharmaceutically acceptable antioxidants, and cosmetic and dermatological light protection formulations having an active content of a combination of at least one substance chosen from the group consisting of 2.4-O-furfurylidenesorbitol and alkyl ethers thereof and at least one substance chosen from the group consisting of cosmetically or pharmaceutically acceptable antioxidants, but in particular active compound combinations comprising a combination of at least one substance chosen from the group consisting of 2.4-O-furfurylidenesorbitol and alkyl ethers thereof and at least one substance chosen from the group consisting of tocopherols and tocopheryl esters, and cosmetic and dermatological light protection formulations having an active content of a combination of at least one substance chosen from the group consisting of 2.4-O-furfurylidenesorbitol and alkyl ethers thereof and at least one substance chosen from the group consisting of tocopherols and tocopheryl esters, remedy the disadvantages of the prior art.

2.4-O-furfurylidenesorbitol is synonymous with the designations 2,4-O-furfurylideneglucitol, 2,4-O-(2-furanylmethylene) glucitol and 2,4-monofurfurylidenesorbitol. It is distinguished by the following structure:

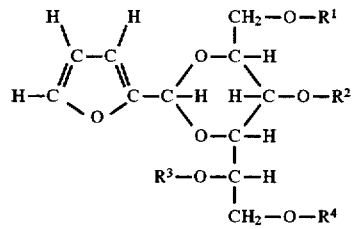

and can be called up in Chemical Abstracts under registry number 7089-59-0.

According to the invention, $R^{1-4}$ independently of one another are H, methyl groups and/or ethyl groups. According to the invention, $R^{1-4}$ are particularly preferably identical and are H or methyl groups (2,4-mono-furfurylidene-tetra-O-methyl-sorbitol).

The configuration of the four asymmetric carbon atoms in the molecular portion derived from sorbitol preferably corresponds to that of the carbon atoms in naturally occurring sorbitol, although the other stereoisomers are also in principle advantageous.

The configuration of the asymmetric carbon atom of the furfurylidene group can equally advantageously be R or S. A racemate of the R and S configuration with respect to this carbon atom is of particular advantage according to the invention.

The antioxidants according to the invention can advantageously be chosen from the group consisting of customary cosmetic and dermatological antioxidants, in particular from the group consisting of tocopherols and derivatives thereof, especially α-tocopherol or α-tocopheryl esters, in particular α-tocopheryl acetate, and furthermore sesamol, bile acid derivatives, such as methyl, ethyl, propyl, amyl, butyl and lauryl gallate, coniferyl benzoate of benzoin resin, nordihydroguaiacum resin acid, nordihydroguaiaretic acid, butyl hydroxyanisole, butyl hydroxytoluene, ascorbic acid, citric acid, phosphoric acid, lecithin, trihydroxybutyrophenone, carotenes, vitamin A and derivatives thereof, in particular retinyl palmitate, ascorbic acid, ascorbyl palmitate, dilauryl thiodipropionate, distearyl thiodipropionate, monoisopropyl citrate, thiodipropionic acid and EDTA and EDTA derivatives.

The antioxidants according to the invention are preferably chosen from the group consisting of tocopherols and derivatives thereof.

Tocopherols, also called vitamin E, are derived from the parent substance tocol ((2-methyl-2-(4,8,12-trimethyltridecyl)-chroman-6-ol) and are characterized by the following structures:

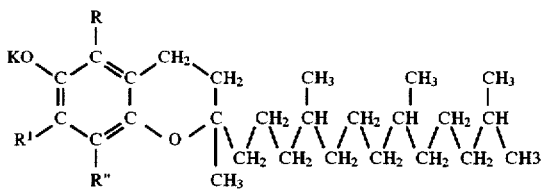

In this formula, K is either H or an acyl radical and R, R' and R" independently of one another are H or a methyl group, for example:

| | |
|---|---|
| R = R' = R" = K = H: | tocol |
| R = R' = R" = methyl, K = H: | α-tocopherol |
| R = R" = methyl, R' = K = H: | β-tocopherol |
| R = R' = R" = methyl, K = —C—CH₃:<br>‖<br>O | α-tocopherol acetate | and other variants. In these esters, for the acyl radical K:

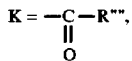

wherein R"" can be an alkyl or alkenyl radical having 1 to 21 atoms. Particularly preferably, R""=methyl.

α-Tocopherol, which occurs most frequently in nature and is the most important, has the configuration 2R, 4'R, 8'R. It is sometimes also called RRR-α-tocopherol.

The tocopherol derivatives which are preferred according to the invention are α-tocopherol and its esters, in particular α-tocopheryl acetate.

It is known from EP Patent Application Specification 345 362 to employ 2,4-furfurylidenesorbitol in cosmetic and dermatological formulations. In such formulations it is primarily used as an agent for trapping free radicals which may be caused, inter alia, by UV radiation.

It is furthermore known from U.S. Pat. Nos. 4,144,325 and 4,248,861 and from numerous other documents to employ vitamin E in cosmetic and dermatological light protection formulations.

However, it was not to be foreseen that the combinations according to the invention of 2,4-O-furfurylidenesorbitol and alkyl ethers thereof and of at least one substance chosen from the group consisting of antioxidants, in particular tocopherols and tocopheryl esters, would, in a synergistic manner, better than the particular individual substances, provide better protection against damage by UV radiation act better as an antioxidant act better as an agent which traps free radicals prevent bonding of harmful photoproducts to lipids, DNA and proteins to a better extent.

Furthermore, it was not to be foreseen that the active compound combinations according to the invention or the cosmetic or dermatological formulations according to the invention would have a sufficiently high stability for use lead to products tolerated by the skin not intervene in microorganism flora endogenous to the skin counteract light-induced ageing of the skin.

In particular, it was not to be foreseen that the active compound combinations according to the invention or the cosmetic or dermatological formulations according to the invention would be distinguished by a pronounced delayed reaction ("retarded action").

The active compound combinations according to the invention or the cosmetic or dermatological formulations according to the invention furthermore are particularly suitable for penetration of lower-lying layers of skin, where they can display their action in an advantageous manner.

The active compound combinations according to the invention or the cosmetic or dermatological formulations according to the invention furthermore are astonishingly suitable for controlled prophylaxis and/or treatment of UV induced skin damage.

The invention accordingly also relates to the use of the active compound combinations according to the invention or the cosmetic or dermatological formulations according to the invention for protecting the skin against the harmful influence of ultraviolet light.

It has been found, astonishingly, that the active compound combinations according to the invention or the cosmetic or dermatological formulations according to the invention are capable of trapping photochemically produced free radicals, providing protection from photochemically induced uncontrolled oxidation processes and even "quenching" singlet oxygen, that is to say converting it into the triplet ground state by a physicochemical process. Substances having this property are also called "quenching agents".

The invention therefore also relates to the use of the active compound combinations according to the invention as an agent which traps free radicals, antioxidant and/or quenching agent for photochemically produced reactive substances, such as singlet oxygen.

The cosmetic and/or dermatological formulations according to the invention can have the customary composition and be used for treatment of the skin and/or hair in the context of dermatological treatment or treatment in the context of care cosmetics. However, they can also be employed in make-up products in decorative cosmetics. They preferably comprise 0.01% by weight to 10% by weight, but in particular 0.1% by weight to 6% by weight, based on the total weight of one or more substances of the group consisting of 2,4-O-furfurylidenesorbitol and alkyl ethers thereof and at least one substance chosen from the group consisting of tocopherol and its esters.

For use, the active compound combinations according to the invention or the cosmetic or dermatological formulations according to the invention are applied to the skin and/or hair in an adequate amount in the manner customary for cosmetics and dermatological agents.

Those cosmetic and dermatological formulations which are in the form of a sunscreen agent are particularly preferred. These preferably additionally comprise at least one UVA filter and/or at least one UVB filter and/or at least one inorganic pigment.

Cosmetic and/or dermatological formulations according to the invention for protecting the skin from UV rays can be in various forms, such as are usually employed, for example, for this type of formulations. They can thus be, for example, a solution, an emulsion of the water-in-oil (W/O) type or of the oil-in-water (O/W) type, or a multiple emulsion, for example of the water-in-oil-in-water (W/O/W) type, a gel, a hydrodispersion, a solid stick or also an aerosol.

The cosmetic formulations according to the invention can comprise cosmetic auxiliaries such as are usually used in such formulations, for example preservatives, bactericides, perfumes, agents for preventing foaming, dyestuffs, pigments which have a colouring action, thickening agents, surface-active substances, emulsifiers, softening substances, moistening and/or humectant substances, fats, oils, waxes or other customary constituents of a cosmetic formulation, such as alcohols, polyols, polymers, foam stabilizers, electrolytes, organic solvents or silicone derivatives.

If the cosmetic or dermatological formulation is a solution or lotion, solvents which can be used are:

water or aqueous solutions;

oils, such as triglycerides of capric or caprylic acid, but preferably castor oil;

mineral oils;

fats, waxes and other naturally occurring and synthetic fatty substances, preferably esters of fatty acids with alcohols of low C number, for example with isopropanol, propylene glycol or glycerol, or esters of fatty alcohols with alkanoic acids of low C number or with fatty acids;

alcohols, diols or polyols of low C number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

Mixtures of the abovementioned solvents are used in particular. In the case of alcoholic solvents, water can be a further constituent.

Emulsions according to the invention, for example in the form of a sunscreen cream, a sunscreen lotion or a sunscreen milk, are advantageous and comprise, for example, the fats, oils, waxes and other fatty substances mentioned, as well as water and an emulsifier, such as is usually used for such a type of formulation.

Hydrodispersions are also advantageous embodiments of the present invention.

Gels according to the invention usually comprise alcohols of low C number, for example ethanol, isopropanol, 1,2-propanediol, glycerol, and water or an abovementioned oil in the presence of a thickening agent which is preferably silicon dioxide or an aluminium silicate in oily-alcoholic gels and preferably a polyacrylate in aqueous-alcoholic or alcoholic gels.

Solid sticks according to the invention comprise for example naturally occurring or synthetic waxes, fatty alcohols or fatty acid esters. Lipcare sticks are preferred.

Suitable propellants for cosmetic or dermatological formulations according to the invention which can be sprayed from aerosol containers are the customary known readily volatile, liquefied propellants, for example hydrocarbons (propane, butane or isobutane), which can be employed by themselves or as a mixture with one another. Compressed air can also advantageously be used.

The expert of course knows that there are nontoxic propellant gases per se which would be suitable in principle for the present invention, but which nevertheless should be dispensed with because of their objectionable action on the environment or other concomitant circumstances, in particular fluorohydrocarbons and fluorochlorohydrocarbons (CFCs).

Advantageous cosmetic and dermatological formulations according to the invention for the protection of the skin comprise the active compound combinations according to the invention in amounts of 0.01–10% by weight, preferably in amounts of 0.1–6% by weight, but in particular 0.1–4% by weight, based on the total weight of the formulation.

The formulations according to the invention can preferably furthermore comprise organic substances which absorb UV radiation in the UVB range, the total amount of filter substances being, for example, 0.1% by weight to 30% by weight, preferably 0.5 to 10% by weight, in particular 1 to 6% by weight, based on the total weight of the formulation, in order to provide cosmetic formulations which protect the skin from the entire range of ultraviolet radiation. They can also be used as sunscreen agents.

The UVB filters can be oil-soluble or water-soluble. Oil-soluble substances which can advantageously be used according to the invention are:

3-benzylidenecamphor derivatives, preferably 3-(4-methylbenzylidene) camphor, 3-benzylidenecamphor;

4-aminobenzoic acid derivatives, preferably 2-ethylhexyl 4-(dimethylamino)benzoate and amyl 4-(dimethylamino)benzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 2-ethylhexyl 4-methoxybenzalmalonate;

2,4,6-trianilino-(p-carbo-2'-ethyl-1'-hexyloxy)-1,3,5-triazine.

Water-soluble substances which can advantageously be used according to the invention are:

salts of 2-phenylbenzimidazole-5-sulphonic acid, such as its sodium, potassium or its triethanolammonium salt, and the sulphonic acid itself;

sulphonic acid derivatives of benzophenones, preferably 2-hydroxy-4-methoxybenzophenone-5-sulphonic acid and their salts;

sulphonic acid derivatives of 3-benzylidenecamphor, such as, for example, 4-(2-oxo-3-bornylidenemethyl)-benzenesulphonic acid, 2-methyl-5-(2-oxo-3-bornylidenemethyl)sulphonic acid and their salts.

The list of UVB filters mentioned which can be used in combination with the active compound combinations according to the invention is of course not intended to be limiting.

The invention also relates to the combination of active compound combinations according to the invention with one or more UVB filters and cosmetic or dermatological formulations according to the invention which also comprise one or more UVB filters.

It may also be advantageous to combine active compound combinations according to the invention with UVA filters which have hitherto usually been contained in cosmetic and/or dermatological formulations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. The invention also relates to these combinations and to formulations comprising these combinations. The amounts used for the UVB combination can be employed.

Advantageous formulations furthermore are obtained when the active compound combinations according to the invention are combined with UVA and UVB filters.

Cosmetic and/or dermatological light protection formulations according to the invention can also comprise inorganic pigments which are usually used in cosmetics for the protection of the skin from UV rays. These are oxides of titanium, zinc, iron, zirconium, silicon, manganese, aluminium, cerium and mixtures thereof, as well as modifications in which the oxides are the active agents. They are particularly preferably pigments based on titanium dioxide.

The invention also relates to these combinations of UVA filter and/or UVB filter and pigment and to formulations comprising this combination. The amounts mentioned for the above combinations can be used.

Cosmetic formulations according to the invention for the protection of hair from UV rays are, for example, shampooing agents, formulations which are used when rinsing the hair before or after shampooing, before or after permanent wave treatment or before or after colouring or bleaching of the hair, formulations for blow-drying or setting hair, formulations for colouring or bleaching, a styling and treatment lotion, a hair spray or permanent wave agents. The cosmetic formulations comprise active compounds and auxiliaries such as are usually used for this type of formulations for hair care and hair treatment. Auxiliaries which are used are preservatives, surface-active substances, substances for preventing foaming, emulsifiers, thickening agents, fats, oils, waxes, organic solvents, bactericides, perfumes, dyestuffs or pigments whose task is to colour the hair or the formulation itself, electrolytes and formulations to counter the hair becoming greasy.

Cosmetic formulations which are a shampooing agent preferably comprise at least one anionic, non-ionic or amphoteric surface-active substance, or mixtures thereof, an active compound combination according to the invention in an aqueous medium, and auxiliaries such as are usually used for this purpose. The surface-active substance can be present in the shampooing agent in a concentration of between 1% by weight and 50% by weight.

If the cosmetic or dermatological formulation according to the invention is in the form of a lotion which is rinsed out and is used, for example, before or after bleaching, before or after shampooing, between two shampooing steps, before or after permanent wave treatment, then it comprises, for example, aqueous or aqueous-alcoholic solutions, which optionally comprise surface-active substances, preferably non-ionic or cationic surface-active substances, the concentration of which can be between 0.1 and 10% by weight, preferably between 0.2 and 5% by weight. This cosmetic or dermatological formulation can also be an aerosol comprising the auxiliaries usually used for this purpose.

A cosmetic formulation in the form of a lotion which is not rinsed out, in particular a lotion for setting hair, a lotion used when blow-drying the hair or a styling and treatment lotion, is in general an aqueous, alcoholic or aqueous-alcoholic solution and comprises at least one cationic, anionic, non-ionic or amphoteric polymer or also mixtures thereof, as well as an active compound combination according to the invention. The amount of polymers used is, for example, between 0.1 and 10% by weight, preferably between 0.1 and 3% by weight.

Cosmetic and dermatological formulations according to the invention for treatment and care of hair which comprise an active compound combination according to the invention can be in the form of emulsions which are of the non-ionic or anionic type. Non-ionic emulsions comprise, in addition to water, oils or fatty alcohols, which, for example, can also be polyethoxylated or polypropoxylated, or also mixtures of the two organic components. These emulsions optionally comprise cationic surface-active substances. Anionic emulsions are preferably of the soap type.

Cosmetic and dermatological formulations for treatment and care of hair can be in the form of gels which, in addition to an active compound combination according to the invention and to solvents usually used for this purpose, also comprise organic thickening agents, for example gum arabic, xanthan gum, sodium alginate, cellulose derivatives, preferably methylcellulose, hydroxymethylcellulose, hydroxyethylcellulose, hydroxypropylcellulose or hydroxypropylmethylcellulose, or inorganic thickening agents, for example aluminium silicates, such as, for example, bentonites, or a mixture of polyethylene glycol and polyethylene glycol stearate or distearate. The gel comprises the thickening agent in an amount of, for example, between 0.1 and 30% by weight, preferably between 0.5 and 15% by weight.

The amount of active compound combinations according to the invention in an agent intended for hair is preferably 0.01% by weight to 10% by weight, in particular 0.5% by weight to 5% by weight, based on the total weight of the formulations.

The present invention also relates to a method for protecting the skin and hair from UVA and UVB radiation, which is characterized in that a cosmetic or dermatological formulation which comprises an active compound combination according to the invention is applied to the skin or hair in an adequate amount, and to the use of these active compound combinations for this purpose.

The present invention also relates to a process for protecting colourless or coloured cosmetic and dermatological formulations from UVA and UVB rays, and to these formulations themselves, which are, for example, the abovementioned formulations for treatment and care of hair, in particular hair colouring agents, hair sprays, shampooing agents, colour shampooing agents, make-up products, such as, for example, nail varnishes, lipsticks, foundations and creams for treatment of the skin, or all other cosmetic formulations whose constituents may give rise to stability problems because of light during storage, characterized in that an active compound combination according to the invention is added to the cosmetic or dermatological formulations in an amount sufficient for stabilization against light.

The amount of active compound combinations according to the invention in these formulations is preferably 0.01% by weight to 10% by weight, in particular 0.1% by weight to 3% by weight, based on the total weight of the formulations.

The invention also relates to the process for the preparation of the cosmetic formulations according to the invention, which is characterized in that active compound combinations according to the invention are incorporated into cosmetic or dermatological formulations in a manner which is known per se.

The following examples are intended to illustrate the present invention without limiting it. The figures relate to percentages by weight, based on the total weight of the formulations.

The following data in the compositions of active compound combinations I–V are based on the total weight of the active compound combinations.

| | % by weight |
|---|---|
| Active compound combination I | |
| Furfurylidenesorbitol | 10.00 |
| Vitamin E acetate | 90.00 |
| Active compound combination II | |
| Furfurylidenesorbitol | 25.00 |
| Vitamin E acetate | 75.00 |
| Active compound combination III | |
| Furfurylidenesorbitol | 50.00 |
| Vitamin E acetate | 50.00 |
| Active compound combination IV | |
| Furfurylidenesorbitol | 75.00 |
| Vitamin E acetate | 25.00 |
| Active compound combination V | |
| Furfurylidenesorbitol | 90.00 |
| Vitamin E acetate | 10.00 |
| Example 1 | |
| Cyclomethicone | 2.000 |
| Cetyldimethicone copolyol | 0.200 |
| PEG 22 dodecyl copolymer | 3.000 |
| Paraffin oil (DAB 9) | 2.000 |
| Caprylic acid/capric acid triglyceride | 5.800 |
| Octyl methoxycinnamate | 5.800 |
| Butyl-methoxy-dibenzoylmethane | 4.000 |
| Active compound combination I | 0.300 |
| ZnSO$_4$ | 0.700 |
| Na$_4$EDTA | 0.300 |
| Perfume, preservative, dyestuffs | as required |
| completely demineralized H$_2$O | to 100.000 |
| Example 2 | |
| Cyclomethicone | 2.000 |
| Cetyldimethicone copolyol | 0.200 |
| PEG 22 dodecyl copolymer | 3.000 |
| Paraffin oil (DAB 9) | 2.000 |
| Caprylic acid/capric acid triglyceride | 5.800 |
| Octyl methoxycinnamate | 5.800 |
| Butyl-methoxy-dibenzoylmethane | 4.000 |
| Active compound combination II | 0.500 |
| ZnSO$_4$ | 0.700 |
| Na$_4$EDTA | 0.300 |
| Perfume, preservative, dyestuffs | as required |
| Completely demineralized H$_2$O | to 100.000 |
| Example 3 | |
| Cyclomethicone | 2.000 |
| Cetyldimethicone copolyol | 0.200 |
| PEG 22 dodecyl copolymer | 3.000 |
| Paraffin oil (DAB 9) | 2.000 |
| Caprylic acid/capric acid triglyceride | 5.800 |
| Octyl methoxycinnamate | 5.800 |
| Butyl-methoxy-dibenzoylmethane | 4.000 |
| Active compound combination III | 2.500 |
| ZnSO$_4$ | 0.700 |
| Na$_4$EDTA | 0.300 |
| Perfume, preservative, dyestuffs | as required |
| Completely demineralized H$_2$O | to 100.000 |
| Example 4 | |
| Cyclomethicone | 2.000 |
| Cetyldimethicone copolyol | 0.200 |
| PEG 22 dodecyl copolymer | 3.000 |
| Paraffin oil (DAB 9) | 2.000 |
| Caprylic acid/capric acid triglyceride | 5.800 |
| Octyl methoxycinnamate | 5.800 |
| Butyl-methoxy-dibenzoylmethane | 4.000 |
| Active compound combination IV | 3.000 |
| ZnSO$_4$ | 0.700 |
| Na$_4$EDTA | 0.300 |
| Perfume, preservative, dyestuffs | as required |
| Completely demineralized H$_2$O | to 100.000 |
| Example 5 | |
| Cyclomethicone | 2.000 |
| Cetearyl alcohol + PEG 40 hydrogenated castor oil + sodium cetearyl sulphate | 2.500 |
| Glyceryl lanolate | 1.000 |
| Caprylic acid/capric acid triglyceride | 0.100 |
| Lauryl methicone copolyol | 2.000 |
| Octyl stearate | 3.000 |
| Castor oil | 4.000 |
| Glycerol | 3.000 |
| Acrylamide/sodium acrylate copolymer | 0.300 |
| Hydroxypropylmethylcellulose | 0.300 |
| Octyl methoxycinnamate | 5.000 |
| Butyl-methoxy-dibenzoylmethane | 0.500 |
| Active compound combination V | 1.750 |
| Na$_3$HEDTA | 1.500 |
| Perfume, preservative, dyestuffs | as required |
| Completely demineralized H$_2$O | to 100.000 |
| Example 6 | |
| Cyclomethicone | 2.000 |
| Cetearyl alcohol + PEG 40 hydrogenated castor oil + sodium cetearyl sulphate | 2.500 |
| Glyceryl lanolate | 1.000 |
| Caprylic acid/capric acid triglyceride | 0.100 |
| Lauryl methicone copolyol | 2.000 |
| Octyl stearate | 3.000 |
| Castor oil | 4.000 |
| Glycerol | 3.000 |
| Acrylamide/sodium acrylate copolymer | 0.300 |
| Hydroxypropylmethylcellulose | 0.300 |
| Octyl methoxycinnamate | 5.000 |
| Butyl-methoxy-dibenzoylmethane | 0.750 |
| Active compound combination I | 2.500 |
| Na$_3$HEDTA | 1.500 |
| Perfume, preservative, dyestuffs | as required |
| Completely demineralized H$_2$O | to 100.000 |
| Example 7 | |
| Cyclomethicone | 2.000 |
| Cetearyl alcohol + PEG 40 hydrogenated castor oil + sodium cetearyl sulphate | 2.500 |
| Glyceryl lanolate | 1.000 |
| Caprylic acid/capric acid triglyceride | 0.100 |
| Lauryl methicone copolyol | 2.000 |
| Octyl stearate | 3.000 |
| Castor oil | 4.000 |
| Glycerol | 3.000 |
| Acrylamide/sodium acrylate copolymer | 0.300 |
| Hydroxypropylmethylcellulose | 0.300 |
| Octyl methoxycinnamate | 5.000 |
| Butyl-methoxy-dibenzoylmethane | 1.000 |
| Active compound combination II | 0.700 |
| Na$_3$HEDTA | 1.500 |
| Perfume, preservative, dyestuffs | as required |
| Completely demineralized H$_2$O | to 100.000 |
| Example 8 | |
| Cyclomethicone | 2.000 |
| Cetearyl alcohol + PEG 40 hydrogenated castor oil + sodium cetearyl sulphate | 2.500 |
| Glyceryl lanolate | 1.000 |
| Caprylic acid/capric acid triglyceride | 0.100 |
| Lauryl methicone copolyol | 2.000 |
| Octyl stearate | 3.000 |
| Castor oil | 4.000 |
| Glycerol | 3.000 |
| Acrylamide/sodium acrylate copolymer | 0.300 |
| Hydroxypropylmethylcellulose | 0.300 |
| Octyl methoxycinnamate | 5.000 |
| Butyl-methoxy-dibenzoylmethane | 0.500 |
| Active compound combination III | 1.600 |
| Na$_3$HEDTA | 1.500 |

| | % by weight |
|---|---|
| Perfume, preservative, dyestuffs | as required |
| Completely demineralized H₂O | to 100.000 |

We claim:

1. Cosmetic or dermatological formulations for the protection of the skin against oxidation processes, comprising the combination of at least one substance selected from the group consisting of 2,4-O-furfurylidenesorbitol and alkyl ethers thereof and more than 0.2% by weight based on the total weight of the formulations, of one or more substances chosen from the group consisting of cosmetically or pharmaceutically acceptable antioxidants, with the proviso that the antioxidants do not include citric acid or citrates.

2. Formulations according to claim 1, wherein the alkyl ether of 2,4-O-furfurylidenesorbitol is 2,4-monofurfurylidene-tetra-O-methyl-sorbitol.

3. Formulations according to claim 1, wherein the cosmetically or pharmaceutically acceptable antioxidants are chosen from the group consisting of tocopherols and derivatives thereof, especially α-tocopherol and α-tocopheryl esters, in particular α-tocopheryl acetate, butyl hydroxyanisole, butyl hydroxytoluene, asorbic acid, trihydroxybutyrophenone, carotenes, vitamin A and derivatives thereof.

4. Formulations according to claim 1, wherein the cosmetically or pharmaceutically acceptable antioxidants are chosen from the group consisting of tocopherols and tocopheryl esters.

5. Formulations according to claim 1, wherein they constitute light protection formulations.

6. A method for protecting skin against oxidation comprising application thereto of a combination of at least one substance selected from the group consisting of 2,4-O-furfurylidenesorbitol and alkyl ethers thereof and one or more substances selected from the group consisting of cosmetically or pharmaceutically acceptable antioxidants, with the proviso that the antioxidants do not include citric acid or citrates for the preparation of cosmetic or pharmaceutical formulations, the proportion by weight of the antioxidant(s) necessarily being more than 0.2% by weight, based on the total weight of the formulations.

7. Formulations according to claim 3, wherein the antioxidants are selected from the group consisting of retinyl palmitate, ascorbyl palmitate, dilauryl thiodipropionte, distearyl thiodipropionate, and thiodipropionic acid.

8. Formulations according to claim 3, wherein the antioxidants are α-tocopherol and α-tocopherol acetate.

* * * * *